United States Patent [19]

Muryobayashi et al.

[11] Patent Number: 4,473,587
[45] Date of Patent: Sep. 25, 1984

[54] PROSTAGLANDIN E₁ ANALOGUES

[75] Inventors: Takashi Muryobayashi, Takatsuki; Katsuhiro Imaki, Tsuzuki; Yoshiki Sakai, Mishima, all of Japan

[73] Assignee: Ono Pharmaceutical Co., Ltd., Osaka, Japan

[21] Appl. No.: 515,909

[22] Filed: Jul. 21, 1983

[30] Foreign Application Priority Data

Jul. 22, 1982 [JP] Japan ............... 57-126665

[51] Int. Cl.³ .................. C07C 177/00; C07C 49/653; A61K 31/559
[52] U.S. Cl. .................. 424/331; 568/367; 536/46; 549/465
[58] Field of Search .......... 568/367; 424/331; 542/426; 536/46

[56] References Cited

FOREIGN PATENT DOCUMENTS 68871 1/1983 European Pat. Off. ............ 568/367

Primary Examiner—Robert Gerstl
Attorney, Agent, or Firm—Stevens, Davis, Miller & Mosher

[57] ABSTRACT

Prostaglandin E₁ analogues of the general formula:

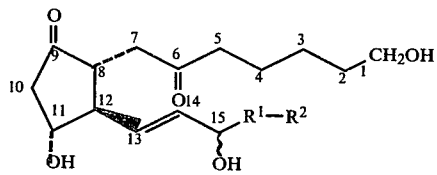

(wherein $R^1$ represents a single bond or a straight- or branched-chain alkylene group of from 1 to 5 carbon atom(s), $R^2$ represents a cycloalkyl group of from 4 to 7 carbon atoms either unsubstituted or substituted by at least one straight- or branched-chain alkyl group of from 1 to 8 carbon(s), and the double bond between $C_{13}$ and $C_{14}$ is trans) and cyclodextrin clathrate thereof, are useful in the prevention or treatment of cytodamage associated with digestive system disease, especially liver damage.

11 Claims, No Drawings

PROSTAGLANDIN E₁ ANALOGUES

This invention is concerned with new prostaglandin E₁ analogues.

Prostaglandins are derivatives of prostanoic acid which has the following formula:

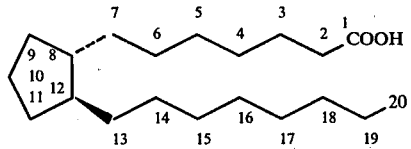

Various types of prostaglandins are known, the types depending inter alia on the structure and substituents on the alicyclic ring. For example, the alicyclic ring of prostaglandin E(PGE) has the structure:

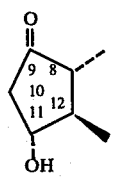

The dotted lines in the foregoing formulae and in other formulae throughout this specification denote, in accordance with generally accepted rules of nomenclature, that the attached grouping lies behind the general plane of the ring system, i.e. that the grouping is in α-configuration, and the thickened lines denote that the grouping lies in front of the general plane of the system, i.e. that the grouping is in β-configuration. The wavy line ~~ in other formulae throughout this specification indicates that the grouping is in α- or β-configuration, or mixtures thereof.

Such compounds are sub-classified according to the position of double bond(s) in the side chain(s) attached to the 8- and 12-positions of the alicyclic ring. Thus PG₁ compounds have a trans- double bond between $C_{13}-C_{14}(\text{trans-}\Delta^{13})$. For example, prostaglandin E₁ (PGE₁) is characterized by the following structure:

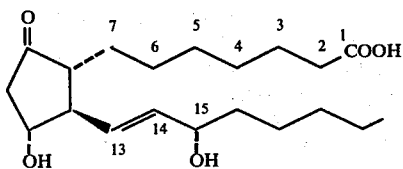

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di- tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE₁ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

Recently it has been found that certain prostaglandin compounds possess a previously unknown activity, in protecting cells in the living body. This activity is name cytoprotective activity. It has been reported that PGE₂ is effective against a diet-induced acute pancreatitis in mice [cf Gastroenterology, 78, 777–781 (1980)] and that 16,16-dimethyl-PGE₂ prevents acute galactosamine-induced liver damage and carbon tetrachloride-induced liver cell necrosis [cf. Folia Histochemica et Cytochemica, 18, 311–318 (1980) and Gastroenterology, 81, 211–217, (1981), respectively].

As a result of research and experimentation to discover novel compounds which have the pharmacological effects of the natural prostaglandins, or which have one or more of these properties to an enhanced degree, or which have properties which are not found with the natural prostaglandins, it has been discovered that novel compounds in which the carboxy group of the 1-position of PGE₁ has been replaced by a hydroxymethyl group, an oxo group has been introduced into the carbon atom at the 6-position, and the n-pentyl group attached to the 15-position is replaced by certain cycloalkyl-substituted alkyl groups, or cycloalkyl groups, have a selective strong cytoprotective activity.

The present invention accordingly provides novel prostaglandin E₁ analogues of the general formula:

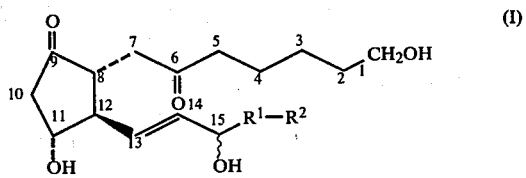

(wherein R¹ represents a single bond or a straight- or branched-chain alkylene group of from 1 to 5 carbon atoms, R² represents a cycloalkyl group of from 4 to 7 carbon atoms either unsubstituted or substituted by at least one straight- or branched-chain alkyl group of from 1 to 8 carbon atoms, and the double bond between $C_{13}$ and $C_{14}$ is trans) and cyclodextrin clathrates thereof.

Preferably the hydroxy group attached to the C-15 carbon atom of formula (I) is in α-configuration.

The present invention is concerned with all compounds of general formula (I) in the 'natural' form or its enantiomeric form, or mixtures thereof, more particularly the racemic form consisting of equimolecular mixtures of natural and its enantiomeric form.

As will be apparent to those skilled in the art, the compounds depicted in general formula (I) have at least four centres of chirality, these four centres of chirality being at the C-8, C-11, C-12 and C-15 carbon atoms. Still further centres of chirality may occur when $R^2$ is an alkylsubstituted cycloalkyl group or $R^1$ is a branched-chain alkylene group. The presence of chirality leads, as is well known, to the existence of isomerism. However, the compounds of general formula (I) all have such a configuration that the side-chains attached to the ring carbon atoms in the positions identified as 8 and 12 are trans with respect to each other. Accordingly, all isomers of general formula (I), and mixtures thereof, which have those side-chains attached to the ring carbon atoms in positions 8 and 12 in the trans configuration and have hydroxy groups as depicted in the 11- and 15- positions are to be considered within the scope of formula (I).

In the compounds of the general formula (I), the grouping —$R^1$—$R^2$ is preferably cyclobutyl, 1-propylcyclobutyl, 1-butylcyclobutyl, 1-pentylcyclobutyl, 2-propylcyclobutyl, 3-ethylcyclobutyl, 3-propylcyclobutyl, cyclopentyl, cyclopentylmethyl, 1-cyclopentylethyl, 2-cyclopentylethyl, 2-ethylcyclopentyl, 2-propylcyclopentyl, 2-butylcyclopentyl, 1-methyl-3-propylcyclopentyl, 2-methyl-3-propylcyclopentyl, 3-methylcyclopentyl, 3-ethylcyclopentyl, 3-propylcyclopentyl, 3-butylcyclopentyl, 3-pentylcyclopentyl, cyclohexyl, 3-ethylcyclohexyl, 4-methylcyclohexyl, 4-ethylcyclohexyl, 4-propylcyclohexyl, 2,6-dimethylcyclohexyl, cyclohexylmethyl, (1-methylcyclohexyl)-methyl, 1-cyclohexylethyl, 2-cyclohexylethyl, 1-methyl-1-cyclohexylethyl or 1-cycloheptylethyl; more preferably —$R^1$—$R^2$ is cyclobutyl, cyclopentyl, 3-methylcyclopentyl, 3-ethylcyclopentyl, 3-propylcyclopentyl, 3-butylcyclopentyl, 3-pentylcyclopentyl, cyclohexyl or 4-propylcyclohexyl; most preferably —$R^1$—$R^2$ is cyclopentyl, 3-methylcyclopentyl, 3-ethylcyclopentyl, 3-propylcyclopentyl, 3-butylcyclopentyl or 3-pentylcyclopentyl.

Prostaglandin $E_1$ analogues of the general formula (I) and cyclodextrin clathrates thereof have strong cytoprotective activity, and have very weak toxicity. The prostaglandin $E_1$ analogues of the general formula (I) and cyclodextrin clathrates thereof may be used in the prevention and/or treatment of many kinds of diseases associated with cytodamage, as follows:

(1) digestive system diseases for example: liver diseases such as hepatitis, fatty liver, liver cirrhosis, liver abscess, and pancreatic diseases such as pancreatitis;

(2) urologic diseases for example: nephropathies such as diabetic nephropathies, cystitis and urethritis;

(3) respiratory tract diseases for example: pneumonia, empyema, and rhinitis;

(4) cardiovascular diseases for example: arrhythmia, cerebral aneurysm and cerebral embolism, (5) hematologic diseases for example: anemia, and (6) other diseases for example: diabetes mellitus, and its complications.

The compounds of the invention may therefore be used in the treatment (including preventive treatment) of diseases associated with cell damage, especially liver disease.

For example, in standard laboratory tests; (i) in carbon tetrachloride-induced liver damage in rats (using the method described in the specification of U.S. patent application Ser. No. 06/478031); 2-decarboxy-2-hydroxymethyl-6-oxo-15-(3(RS)-butyl-1(S)-cyclopentyl)-16,17,18,19,20-pentanor-$PGE_1$ (referred to as compound A hereafter) produced 71.8% and 53.6% inhibitions of plasma GOT (glutamic oxaloacetic transaminase) and GPT (glutamic pyruvic transaminase), respectively, by oral administration at the dose of 100 μg/kg animal body weight in comparison with controls, and produced 56.6% and 58.8% inhibitions of plasma GOT and GPT, respectively, by oral administration at the dose of 20 μg/kg animal body weight in comparison with controls; 2-decarboxy-2-hydroxymethyl-6-oxo-15-(3(RS)-propyl-1(S)-cyclopentyl)-16,17,18,19,20-pentanor-$PGE_1$ (referred to as compound B hereafter) produced 29.6% and 21.5% inhibitions of plasma GOT and GPT, respectively, by oral administration at the dose of 50 μg/kg animal body weight in comparison with controls; and 2-decarboxy-2-hydroxymethyl-6-oxo-15-cyclopentyl-16,17,18,19,20-pentanor-$PGE_1$ (referred to as compound C hereafter) produced 7.9% and 29.9% inhibitions of plasma GOT and GPT, respectively, by oral administration at the dose of 200 μg/kg animal body weight in comparison with controls;

(ii) in α-naphthylisothiocyanate-induced liver damage in rats (using the method described in the specification of U.S. patent application Ser. No. 06/478031) compound B produced 52.6%, 62.5% and 30.3% inhibitions of plasma GOT, GPT and bilirubin, respectively, by oral administration at the dose of 100 μg/kg animal body weight in comparison with controls, and (iii) in D(+)-galactosamine-induced liver damage in rats (using the method described in the specification of U.S. patent application Ser. No. 06/478031, except that the doses of D(+)-galactosamine were 375 mg/kg animal body weight administered twice at 6 hr intervals by intraperitoneal injection, and the compounds of the present invention were administered orally five times, at 6, 12, 24, 30 and 36 hrs after the first dosage, and blood was gathered 48 hrs after the first dosage of the D(+)-galactosamine), compound A produced 20.4%, 45.1% and 36.2% inhibitions of plasma GOT, GPT and bilirubin, respectively, by oral administration at the dose of 100 μg/kg animal body weight in comparison with control, respectively; and compound B produced 40.0%, 50.3% and 44.2% inhibitions of plasma GOT, GPT and bilirubin, respectively, by oral administration at the dose of 100 μg/kg animal body weight in comparison with control.

In addition to their valuable cytoprotective activity the compounds of the present invention possess relatively weak other prostaglandin-like activities such as hypotensive activity and uterine contractile activity. For example, in standard laboratory tests, (i) compound A and compound B stimulated uterine contraction in the pregnant female rat when administered intravenously on the 20th day of gestation at the doses of 50 and 20 μg/kg animal body weight; and (ii) by intravenous administration to the allobarbital anesthetized dog, compound B produced falls in blood pressure of 13 and 31 mmHg lasting 17 and 37 minutes at the doses of 1 and 2 μg/kg animal body weight, respectively.

In the use of the compounds of the present invention in the treatment of cytodamage, cytoprotective activity i.e. inhibitory activity of cytodamage is the desired pharmacological property, whereas hypotensive activity, platelet aggregation inhibitory activity and uterine contractile activity (which activities are known activities that prostaglandins generally possess) are undesired side-effects.

In comparison with known prostaglandin compounds which have certain structural features in common with the novel compounds of the present invention the latter exhibit as advantageous, more selective cytoprotective activity (i.e. exhibit a lower level of undesired side effects in comparison with the desired cytoprotective activity). It will be understood that the known 6-oxo-ω-cycloalkyl-PGE$_1$ compounds disclosed in our British Patent Publication No. 2,006,753 and 6-oxo-PGE$_1$ alcohol disclosed in British Pat. No. 1,565,605, with which the compounds of the present invention are compared in the following, have not hitherto been disclosed as possessing cytoprotective activity.

In the following Table, the pharmacological activities, i.e. carbon tetrachloride-induced cytodamage inhibition as an example of cytoprotective activity, and hypotensive and platelet aggregation inhibition activities as examples of side-effects, of known compounds are compared with those of compounds A, B and C of the invention.

In the Table, the values of side-effects are indicated relative to the activity of PGE$_1$, taken as 1.00.

TABLE

| cpd. | Doses (μg/Kg) route | CCl$_4$-induced liver damage in the rat Inhibition rates (%) GOT | GPT | side-effects Hypotensive effect[2] (E$_1$ = 1) | Platelet aggregation inhibition[3] (E$_1$ = 1) |
|---|---|---|---|---|---|
| A | 100 (p.o.) | 71.8 | 53.6 | 1.2 | 0.05 |
|   | 20 (p.o.) | 56.6 | 58.8 |   |   |
| B | 50 (p.o.) | 29.6 | 21.5 | 0.35 | 0.05 |
| C | 200 (p.o.) | 7.9 | 29.9 | 0.77 | — |
| D | 100 (p.o.) | 32.6 | 44.5 | 13 | 48.4 |
| E | 100 (p.o.) | 77.0 | 51.5 | 25.7 | 58.6 |
| F | 100 (p.o.) | 62.7 | 55.1 | 12.6 | 51.0 |
| G | 50 (p.o.) | 48.5 | 45.1 | 6.2 | 19.7 |
| H | 100 (p.o.) | 3.4 | −0.07 | — | — |

[1]The method used was that described in the specification of U.S. Pat. Application No. 06/478031.
[2]By intravenous administration to the allobarbital anesthetised dog.
[3]Inhibition of adenosine diphosphate-induced blood platelet aggregation in platelet-rich plasma of rats.
A: 2-Decarboxy-2-hydroxymethyl-6-oxo-15-(3RS-butyl-1S-cyclopentyl)-16,17,18,19,20-pentanor-PGE$_1$
B: 2-Decarboxy-2-hydroxymethyl-6-oxo-15-(3RS-propyl-1S-cyclopentyl)-16,17,18,19,20-pentanor-PGE$_1$
C: 2-Decarboxy-2-hydroxymethyl-6-oxo-15-cyclopentyl-16,17,18,19,20-pentanor-PGE$_1$
[Above compounds A, B and C are compounds of the present invention.]
D: 6-Oxo-15-(3RS-propyl-1RS-cyclopentyl)-16,17,18,19,20-pentanor-PGE$_1$
E: 6-Oxo-15-(3RS-propyl-1RS-cyclopentyl)-16,17,18,19,20-pentanor-PGE$_1$ methyl ester
F: 6-Oxo-15-(3RS-butyl-1RS-cyclopentyl)-16,17,18,19,20-pentanor-PGE$_1$ methyl ester
G: 6-Oxo-15-(4RS-propyl-1RS-cyclohexyl)-16,17,18,19,20-pentanor-PGE$_1$ methyl ester
[Above compounds D, E, F and G are the compounds disclosed as Example compounds in the specification of our British Patent Publication No. 2,006,753.]
H: 2-Decarboxy-2-hydroxymethyl-6-oxo-PGE$_1$
[Above compound H is the compound disclosed as an Example compound in the specification of British Patent No. 1,565,604.]

As is to be noted from the Table, the compounds included in the present invention, i.e. the compounds A, B and C, and the known compounds D, E, F and G are shown to possess cytoprotective activity.

However, compounds A, B and C of the present invention possess very weak side-effects i.e. hypotensive activity and platelet aggregation inhibiting activity, in comparison with the known compounds D, E, F and G and are therefore preferable for use in the treatment of cytodamage.

The compounds A, B and C are superior in their cytoprotective activity to the known compound H.

It will be seen, therefore, that the novel compounds of the invention which have unexpectedly been found to possess cytoprotective activity, also possess superior activity and/or selectivity in comparison witth the known compounds described above (which were not hitherto known to possess cytoprotective activity).

The toxicities of the compounds of the present invention (expressed as the LD$_{50}$) have been found to be more than 10 mg/kg animal body weight by oral administration. Therefore, the compounds of the present invention may be considered to be sufficiently safe and suitable for medical use.

For example, in a test for acute toxicity in mice by oral administration, compound A (i.e. 2-decarboxy-2-hydroxymethyl-6-oxo-5-(3RS-butyl-1S-cyclopentyl)-16,17,18,19,20-pentanor-PGE$_1$) caused no deaths in 5 cases at the dose of 10 mg/kg animal body weight; compound B (i.e. 2-decarboxy-2-hydroxymethyl-6-oxo-15-(3RS-propyl-1S-cyclopentyl)-16,17,18,19,20-pentanor-PGE$_1$) caused two deaths in 5 cases at the dose of 10 mg/kg animal body weight; and compound C (i.e. 2-decarboxy-2-hydroxymethyl-6-oxo-15-cyclopentyl-16,17,18,19,20-pentanor-PGE$_1$) caused no deaths in 5 cases at the dose of 10 mg/kg animal body weight.

According to a feature of the present invention, prostaglandin E$_1$ analogues of the general formula (I) may be prepared by the hydrolysis, under acidic condition, of a compound of general formula:

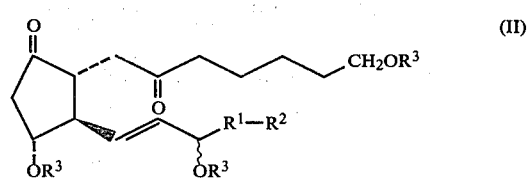

(II)

wherein R$^3$ represents a tetrahydropyran-2-yl, or tetrahydrofuran-2-yl group, either unsubstituted or substituted by at least one alkyl group, or a 1-ethoxyethyl group, and the other symbols are as hereinbefore defined.

The hydrolysis may be carried out, for example, (1) with an aqueous solution of an organic acid such as acetic acid, propionic acid, oxalic acid or p- toluene-sulphonic acid, or an aqueous solution of an inorganic acid, such as hydrochloric acid or sulphuric acid, advantageously in the presence of an inert organic solvent miscible with water, e.g. a lower alkanol such as methanol or ethanol (preferably methanol), or an ether such as 1,2-dimethoxyethane, dioxane or tetrahydrofuran (preferably tetrahydrofuran), at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° C. to 45° C. Advantageously the mild hyrdrolysis may be carried out with a mixture of hydrochloric acid, water and tetrahydrofuran, a mixture of hydrochloric acid, water and methanol, a mixture of acetic acid, water and tetrahydrofuran, or a mixture of p-toluenesulphonic acid and methanol.

Compounds of general formula (II) may be prepared by mild oxidation of a compound of general formula:

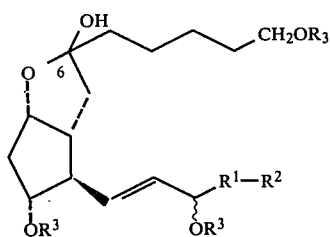
(III)

(wherein the absolute configuration of the substituents on the 6-position carbon atom is S or R or an RS mixture, and the other symbols are as hereinbefore defined), which compound is in equilibrium with its tautomer of the general formula:

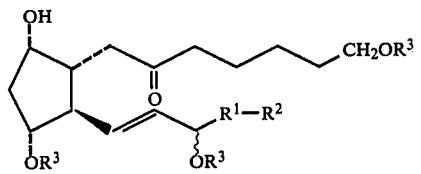
(IV)

wherein the various symbols are as hereinbefore defined.

Preferably the oxidation is carried out under mild, neutral conditions, for example, by reaction with (1) dimethylsulphide-N-chlorosuccinimide complex, thioanisole-N-chlorosuccinimide complex, dimethyl sulphide-chlorine complex or thioanisole-chlorine complex in a haloalkane, e.g. chloroform, methylene chloride or carbon tetrachloride, or toluene at a temperature of from −30° C. to 0° C. [cf. J. Am. Chem. Soc., 94, 7586 (1972)], (2) chromium trioxide-pyridine complex, e.g. Collins reagent, in a haloalkane, e.g. chloroform, methylene chloride or carbon tetrachloride, at a temperature of from 0° C. to ambient, preferably at 0° C., or (3) Jones reagent in the presence of acetone and dilute sulphuric acid at a temperature of from 0° to ambient.

Compounds of the general formula (III) and of the general formula (IV) may be prepared by dehydrobromination and partial hydrolysis of compounds of general formula:

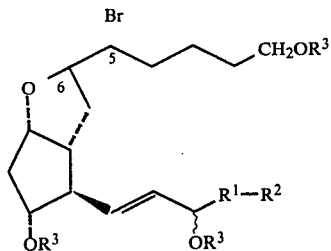
(V)

wherein the absolute configurations of the substituents on the 5-position and 6-position carbon atoms are, independently, S or R or an RS mixture and the other symbols are as hereinbefore defined.

The dehydrohalogenation may be carried out with a known dehydrohalogenation reagent, for example, a bicycloamide such as DBU (i.e. 1,5-diazabicyclo[5.4.-0]undecene-5), DBN (i.e. 1,5-diazabicyclo[4.3.0]nonene-5) or DABCO (i.e. 1,4-diazabicyclo[2.2.2]octane), or an alkali metal, e.g. sodium or potassium, lower alkoxide. The reaction may be carried out at a temperature of from 40° C. to 110° C., preferably at a temperature of from 40° C. to 80° C. When the reagent used is a bicycloamine, it may be carried out with or without solvent, preferably without solvent or with toluene or benzene as solvent. When the reagent used is a lower alkoxide the reaction is preferably conducted using as solvent the corresponding lower alcohol.

The partial hydrolysis must be carried out carefully to avoid elimination of the groups $R^3$, and may be carried out with an aqueous solution of an organic acid, e.g. acetic acid, propionic acid, oxalic acid or p-toluenesulphonic acid, or an aqueous solution of an inorganic acid, e.g. hydrochloric or sulphuric acid, in the presence or absence of an inert organic solvent miscible with water, e.g. an ether such as 1,2-dimethoxyethane, dioxane or tetrahydrofuran (preferably tetrahydrofuran), at a temperature of from 0° C. to 75° C. (preferably from 0° C. to ambient). Advantageously the hydrolysis may be carried out with a mixture of acetic acid, water and tetrahydrofuran, a mixture of dilute hydrochloric acid and tetrahydrofuran, or dilute hydrochloric acid. The progress of the hydrolysis is preferably monitored by thin layer chromatography to avoid elimination of the groups $R^3$.

Compounds represented by the general formula (V) may be prepared by converting to a group $OR^3$, the hydroxy group in the 1-position of a compound of general formula:

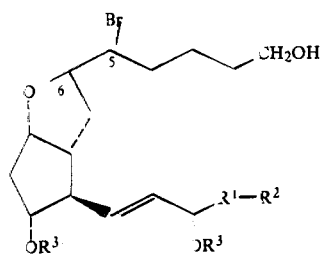
(VI)

wherein the absolute configurations of the substituents on the 5-position and the 6-position of the carbon atoms are, independently, S or R or an RS mixture and the other symbols are as hereinbefore defined.

This reaction is known, and may be carried out in an inert organic solvent, for example, methylene chloride, chloroform, diethyl ether, in the presence of a condensing agent, for example, p-toluenesulphonic acid, sulphuric acid, hydrochloric acid, trifluoroacetic acid, trifluoroborane etherate, phosphorus oxychloride or camphorsulphonic acid, using a 2,3-dihydropyran, 2,3-dihydrofuran or ethyl vinyl ether, at a temperature of from ambient to −30° C.

The compound of general formula (VI) may be prepared by reducing a compound of general formula

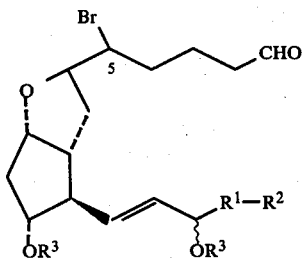

(VII)

(wherein the absolute configurations of the substituents on the 5-position and 6-position carbon atoms are, independently, S or R or an RS mixture, and the other symbols are as hereinbefore defined) to convert the group —CHO to —CH$_2$OH.

This reduction may be carried out, for example, in an inert organic solvent, e.g. tetrahydrofuran, methylene chloride, methanol or ethanol, using sodium borohydride, at a temperature of from −20° C. to 40° C. Preferably, it is carried out with sodium borohydride in methanol or ethanol with cooling by ice.

Compounds of general formula (VII) may be prepared by reducing a compound of general formula:

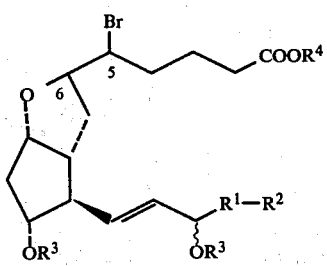

(VIII)

(wherein the absolute configurations of the substituents on the 5-position and the 6-position carbon atoms are, independently, S or R or an RS mixture and R$^4$ represents a straight- or branched-chain alkyl group of from 1 to ............................ carbon other symbols are as hereinbefore defined) tO convert the group —COOR$^4$ to —CHO.

This reduction may be carried out, for example, in hexane, tetrahydrofuran or toluene, using diisobutylaluminium hydride (DIBAL) and an alcohol, for example, methanol or ethanol, at a temperature of from 0° C. to −80° C., preferably, in toluene using DIBAL and methanol at −78° C.

Compounds of the general formula (VI) may also be obtained directly from the compounds of the general formula (VIII) by reduction.

This reduction is well known, and may be carried out by the method of preparation previously described for the preparation of compounds of the general formula (VII) from the compounds of the general formula (VIII).

Compounds of the general formula (VIII) may be prepared by the method described in the specifications of W. German Patent Publication No. 2,803,638 and U.S. Pat. No. 4,178,367.

Compounds of the general formula (VII) may be prepared by the method described in the specification of European Patent Publication No. 68,871; compounds wherein the grouping —R$^1$—R$^2$ represents a cyclopentyl, 3-propylcyclopentyl and 3-butylcyclopentyl group and R$^3$ represents a tetrahydropyran-2-yl group are described in the Reference Examples 6(b), 6 and 6(a), respectively.

Furthermore, the compounds of the present invention of the general formula (I) may also be prepared by hydrolysis, under acidic conditions of the compounds of general formula:

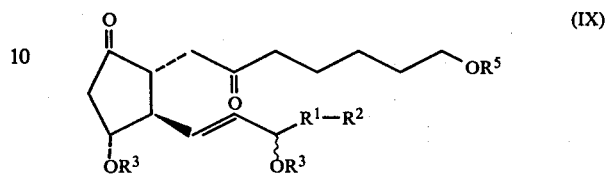

(IX)

(wherein R$^5$ represents a triphenylmethyl group, or a tetrahydropyran-2-yl or tetrahydrofuran-2-yl group, either unsubstituted or substituted by at least one alkyl group, or a 1-ethoxyethyl group, and the other symbols are as hereinbefore defined).

The hydrolysis may be carried out by the method hereinbefore described for the preparation of the compounds of the general formula (I) from the compounds of the general formula (II).

The compounds of the general formula (IX) may be prepared by the series of reactions depicted schematically below in scheme A, wherein X represents an iodine or bromine atom and the other symbols are as hereinbefore defined

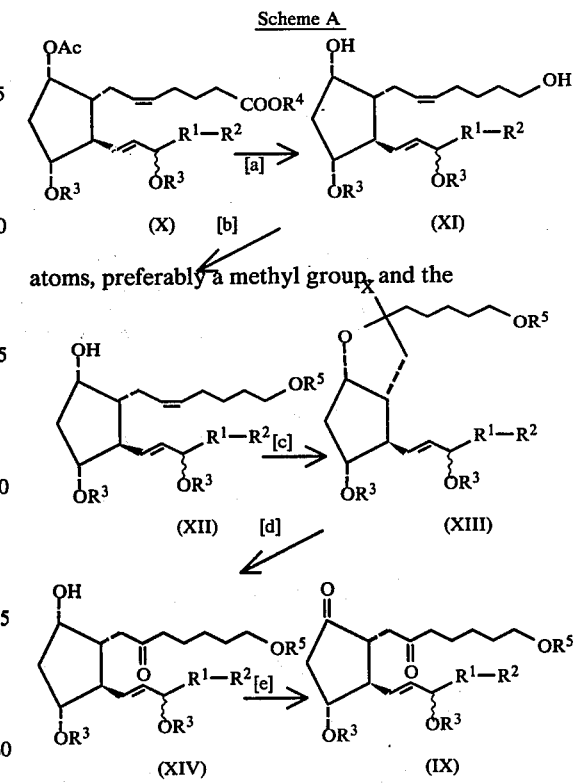

atoms, preferably a methyl group, and the

All of the reaction steps in Scheme A may be conducted by known methods. For example, the step [a] may be conducted by reaction with lithium aluminium hydride, in an ether such as diethyl ether or tetrahydrofuran, at from room temperature to the reflux temperature of the reaction mixture.

The step [b] may be conducted; (1) when $R^5$ is a triphenylmethyl group, by reaction with triphenylmethyl chloride in a tertiary amine such as pyridine, at a temperature of from 0° C. to 50° C.; (2) when $R^5$ is a tetrahydropyran-2-yl or tetrahydrofuran-2-yl group, either unsubstituted or substituted by at least one alkyl group, or a 1-ethoxyethyl group, the hydroxymethyl group attached to the 1-position of the compounds of the general formula (XI) is suitable converted to a group —$CH_2OR^5$ in which $R^5$ is other than triphenylmethyl by reaction in an inert organic solvent such as methylene chloride, chloroform or diethyl ether, in the presence of a condensing agent such as p-toluenesulphonic acid, sulphuric acid or hydrochloric acid, with a 2,3-dihydropyran or 2,3-dihydrofuran, or with ethyl-vinyl ether, at a temperature of from room temperature to −30° C.

Step [c] may be conducted; (1) when X is an iodine atom, by reaction with iodine, in an inert organic solvent such as methylene chloride or chloroform, in the presence of a bicarbonate of an alkali metal such as sodium or potassium at a temperature of from −20° C. to 40° C.; (2) when X is a bromine atom, by reaction with N-bromosuccinimide (NBS) in an aprotic solvent such as methylene chloride or tetrahydropyran, at a temperature of from room temperature to 0° C.

The step [d] may be carried out by the method hereinbefore described for preparing the compounds of the general formula (IV) from the compounds of the general formula (V).

The step [e] may be carried out by the method hereinbefore described for preparing the compounds of the general formula (II) from the compounds of the general formula (IV).

The products obtained in steps [a] to [e] may be used without purification, in subsequent steps.

The compounds of the general formula (X) may be obtained by the methods described in British Patent specification No. 1545213.

Cyclodextrin clathrates of the prostaglandin $E_1$ analogues of the general formula (I) may be prepared using α, β- or γ-cyclodextrin or mixtures thereof, by the process described in the specifications of U.S. Pat. Nos. 3,816,393 and 4,054,736.

Conversion into their cyclodextrin clathrates serves to increase the stability and the water-solubility of the prostaglandin $E_1$ analogues; cyclodextrin clathrates are preferred for pharmaceutical use.

Preferred compounds included in the compounds of the general formula (I) are, for example:

2-decarboxy-2-hydroxymethyl-6-oxo-15-cyclobutyl-16,17,18,19,20-pentanor-PGE$_1$,
2-decarboxy-2-hydroxymethyl-6-oxo-15-cyclopentyl-16,17,18,19,20-pentanor-PGE$_1$,
2-decarboxy-2-hydroxymethyl-6-oxo-15-(3-methylcyclopentyl)-16,17,18,19,20-pentanor-PGE$_1$,
2-decarboxy-2-hydroxymethyl-6-oxo-15-(3-ethylcyclopentyl)-16,17,18,19,20-pentanor-PGE$_1$,
2-decarboxy-2-hydroxymethyl-6-oxo-15-(3-propylcyclopentyl)-16,17,18,19,20-pentanor-PGE$_1$,
2-decarboxy-2-hydroxymethyl-6-oxo-15-(3-butylcyclopentyl)-16,17,18,19,20-pentanor-PGE$_1$,
2-decarboxy-2-hydroxymethyl-6-oxo-15-(3-pentylcyclopentyl)-16,17,18,19,20-pentanor-PGE$_1$,
2-decarboxy-2-hydroxymethyl-6-oxo-15-cyclohexyl-16,17,18,19,20-pentanor-PGE$_1$ and
2-decarboxy-2-hydroxymethyl-6-oxo-15-(4-propylcyclohexyl)-16,17,18,19,20-pentanor-PGE$_1$, and cyclodextrin clathrates thereof.

2-Decarboxy-2-hydroxymethyl-6-oxo-15-(3-propylcyclopentyl)-16,17,18,19,20-pentanor-PGE$_1$,
2-decarboxy-2-hydroxymethyl-6-oxo-15-(3-butylcyclopentyl)-16,17,18,19,20-pentanor-PGE$_1$, and
2-decarboxy-2-hydroxymethyl-6-oxo-15-cyclopentyl-16,17,18,19,20-pentanor-PGE$_1$, and cyclodextrin clathrates thereof are especially preferred.

The following Reference Examples and Examples illustrate the preparation of compounds of the present invention. In the Reference Examples and Examples, 'mp', 'TLC', 'IR', 'NMR' and 'MS' represent 'Melting point', 'Thin layer chromatography', 'Infrared absorption spectrum', 'Nuclear magnetic resonance spectrum' and 'Mass spectrum', respectively. Where solvent ratios are specified in chromatographic separations, the ratios are by volume: the solvents in parentheses in thin layer chromatography show the developing solvents used. Except when specified otherwise, infrared spectra are recorded by the liquid film methods and nuclear magnetic resonance spectra are recorded in deuterochloroform (CDCl$_3$) solution.

REFERENCE EXAMPLE 1

5RS-bromo-6,9α-epoxy-11α,15S-bis(tetrahydropyran-2-yloxy)-15-(3RS-propyl-1S-cyclopentyl)-16,17,18,19,20-pentanorprost-trans-13-en-1-ol To a solution of 0.70 g of 5RS-bromo-6,9α-epoxy-11α,15S-bis(tetrahydropyran-2-yloxy)-16,17,18,19,20-pentanorprost-trans-13-en-1-aldehyde (prepared by the method described in Reference Example 6 in the specification of European patent publication No. 68,871) in 7 ml of ethanol, 50 mg of sodium borohydride was added whilst cooling with ice, and the mixture was stirred for 1 hr. The reaction mixture was diluted with ethyl acetate, and the diluted solution was washed successively with dilute hydrochloric acid, an aqueous solution of sodium bicarbonate and a saturated aqueous solution of sodium chloride, dried over anhydrous magnesium sulphate and concentrated under reduced pressure. The residue was purified by column chromatography on silica gel using a mixture of cyclohexane and ethyl acetate (2:1) as eluent to give 0.552 g of the title compound in a 72.5% yield, having the following physical characteristics:

TLC (cyclohexane:ethyl acetate=1:1): Rf=0.36.
NMR: δ=5.7–5.3(2H,m), 4.7(2H, m), 4.55(1H, m), 0.9(3H, m).
IR: ν=3450, 1022, 980 cm$^{-1}$.
MS: m/e=524, 506, 480, 440, 422, 396.

The following compounds were obtained by the same procedure as Reference Example 1:

(a)

5RS-bromo-6,9α-epoxy-11α,15S-bis(tetrahydropyran-2-yloxy-15-(3RS-butyl-1S-cyclopentyl)-16,17,18,19,20-pentanorprost-trans-13-en-1-ol Starting material: 0.884 g of 5RS-bromo-6,9α-epoxy-11α,15S-bis(tetrahydropyran-2-yloxy)-15-(3-butylcyclopentyl)-16,17,18,19,20-pentanorprost-trans-13-en-1-aldehyde (prepared by the method described in Reference Example 6(a) in the specification of European patent publication No. 68,871);

Yield: 0.836 g (94.5%).

TLC (ethyl acetate:cyclohexane=1:1): Rf=0.29 and 0.35.

NMR: δ=5.7–5.2(2H, m), 4.8–4.4(3H, m) 0.89(3H, m).

IR: ν=3450, 1020, 980 cm$^{-1}$.

MS: m/e=523, 521, 456, 454, 438, 436, 414, 412, 331, 329.

(b)

5RS-bromo-6,9α-epoxy-11α,15S-bis(tetrahydropyran-2-yloxy)-15-cyclopentyl-16,17,18,19,20-pentanorprost-trans-13-en-1-ol Starting material: 818 mg of 5RS-bromo-6,9α-epoxy-11α,15S-bis(tetrahydropyran-2-yloxy)-15-cyclopentyl-16,17,18,19,20-pentanorprost-trans-13-en-1-aldehyde (prepared by the method described in Reference Example 6(b) in the specification of European patent publication No. 68,871);

Yield: 730 mg.

TLC (cyclohexane:ethyl acetate=1:1): Rf=0.25 and 0.32.

NMR: δ5.65–5.25(2H, m), 4.68(2H, m), 4.55(1H, m), 4.17(1H, m), 3.67 (2H, t), 3.48(2H, m).

IR: ν3600–3100, 2929, 2840, 1445, 1200, 1120 cm$^{-1}$.

MS: m/e-438, 398, 382, 380, 356, 354, 319.

REFERENCE EXAMPLE 2

1,11α,15S-tris(tetrahydropyran-2-yloxy)-5RS-bromo-6,9α-epoxy-15-(3RS-propyl-1S-cyclopentyl)-16,17,18,19,20-pentanorprost-trans-13-ene To a mixture of 0.62 g of 5RS-bromo-6,9α-epoxy-11α,15S-bis(tetrahydropyran-2-yloxy)-15-(3RS-propyl-1S-cyclopentyl)-16,17,18,19,20-pentanorprost-trans-13-en-1-ol (prepared in Reference Example 1), 0.10 ml of dihydropyran and 8 ml of methylene chloride, a catalytic amount of p-toluenesulphonic acid was added whilst cooling with ice. The mixture was allowed to warm to room temperature, and stirred for 30 min. To the solution, pyridine was added in order to quench the reaction, and the solution was diluted with diethyl ether. The diluted solution was washed with water and a saturated aqueous solution of sodium chloride, dried over anhydrous magnesium sulphate and concentrated under reduced pressure. The residue was purified by column chromatography on silica gel using a mixture of cyclohexane and ethyl acetate (5:1) as eluent to give 0.63 g of the title compound, in a 89.1% yield, having the following physical characteristics:

(TLC (cyclohexane:ethyl acetate=2:1): Rf=0.35 and 0.41.

NMR: δ=5.7–53.(2H, m), 4.6(3H, m), 0.9(3H, m).

IR: ν=1201, 1034, 1020, 978 cm$^{-1}$.

MS: m/e=625, 608, 524, 480, 440.

The following compounds were obtained by the same procedure as Reference Example 2:

(a)

1,11α,15S-tris(tetrahydropyran-2-yloxy)-5RS-bromo-6,9α-epoxy-15-(3RS-butyl-1S-cyclopentyl)-16,17,18,19,20-pentanorprost-trans-13-ene Starting material: 0.817 g of 5RS-bromo-6,9α-epoxy-11α,15S-bis(tetrahydropyran-2-yloxy)-15-(3RS-butyl-1S-cyclopentyl)-16,17,18,19,20-pentanorprost-13-en-1-ol (prepared in Reference Example 1(a));

Yield: 0.662 g (72%).

TLC (cyclohexane:ethyl acetate=2:1): Rf=0.28.

NMR: δ=5.7–5.2(2H, m), 4.8–4.4(4H, m), 0.89(3H, m).

IR: ν=1202, 1020, 980 cm$^{-1}$.

MS: m/e=540, 538, 522, 520, 496, 494, 403, 401.

(b)

1,11α,15S-tris(tetrahydropyran-2-yloxy)-5RS-bromo-6,9α-epoxy-15-cyclopentyl-16,17,18,19,20-pentanorprost-trans-13-ene Starting material: 720 mg of 5RS-bromo-6,9α-epoxy-11α,15S-bis(tetrahydropyran-2-yloxy)-15-cyclopentyl-16,17,18,19,20-pentanorprost-trans-13-en-1-ol (prepared in Reference Example 1(b));

Yield: 691 mg (84.1%).

TLC (ethyl acetate:cyclohexane=1:1): Rf=0.5 and 0.59.

NMR: δ=5.65–5.26(2H, m), 4.68(2H, m) 4.58(2H, m).

IR: ν=2940, 2860, 1450, 1440, 1350, 1200, 1130 cm$^{-1}$.

MS: m/e=449, 483, 482, 464, 440, 438, 400, 398.

REFERENCE EXAMPLE 3

1,11α,15S-tris(tetrahydropyran-2-yloxy)-9α-hydroxy-15-(3RS-propyl-1S-cyclopentyl-16,17,18,19,20-pentanorprost-trans-13-en-6-one A mixture of 0.61 g of 1,11α,15S-tris(tetrahydropyran-2-yloxy)-5RS-bromo-6,9α-epoxy-15-(3RS-propyl-1S-cyclopentyl)-16,17,18,19,20-pentanorprost-trans-13-ene (prepared in Reference Example 2), 1.28 ml of DBU (1,5-diazabicyclo[5.4.0]undecene-5) and 0.98 ml of toluene was stirred for 16 hrs at 50° C. and then for 3 hrs at 80° C. After the reaction, the mixture was diluted with cold diethyl ether, and the diluted solution was shaken well with cold 1N hydrochloric acid. The oily layer which separated was washed successively with water, an aqueous solution of sodium bicarbonate, and a saturated aqueous solution of sodium chloride, dried over anhydrous magnesium sulphate and concentrated under reduced pressure. The residue was purified by column chromatography on silica gel using a mixture of cyclohexane and ethyl acetate (4:1→2:1) as eluent to give 0.50 g of the title compound in a 88.8% yield, having the following physical characteristics:

TLC (cyclohexane:ethyl acetate=1:1): Rf=0.27.

NMR: δ=5.7–5.2(2H, m), 4.8–4.4(3H, m), 0.9(3H, m).

IR: ν3400, 1700, 1020, 980 cm$^{-1}$.

MS: m/e=630, 545, 530, 461, 445, 426.

The following compounds were obtained by the same procedure as Reference Example 3:

(a)

1,11α,15S-tris(tetrahydropyran-2-yloxy)-5RS-bromo-6,9α-epoxy-15-(3RS-butyl-1S-cyclopentyl)-16,17,18,19,20-pentanorprost-trans-13-en-6-one Starting material: 0.642 g of 1,11α,15S-tris(tetrahydropyran-2-yloxy)-5RS-bromo-6,9α-epoxy-15-(3RS-butyl-1S-cyclopentyl)-16,17,18,19,20-pentanorprost-trans-13-ene (prepared in Reference Example 2(a));

Yield: 0.488 g (83.9%).

TLC (cyclohexane:ethyl acetate=1:1): Rf=0.38;

NMR: δ=5.7–5.2(2H, m), 4.8–4.5(3H, m), 0.89(3H, m).

IR: ν=3450, 1710(weak), 1020, 985 cm$^{-1}$.

MS: m/e=644, 558, 545, 475, 459, 440.

(b)

1,11α,15S-tris(tetrahydropyran-2-yloxy)-9α-hydroxy-15-cyclopentyl-16,17,18,19,20-pentanorprost-trans-13-en-6-one Starting material: 691 mg of 1,11α,15S-tris(tetrahydropyran-2-yloxy)-5RS-bromo-6,9α-epoxy-15-cyclopentyl-16,17,18,19,20-pentanorprost-trans-13-ene (prepared in Reference Example 2(b));

Yield: 514 mg (82.0%).
TLC (ethyl acetate:cyclohexane=1:1): Rf=0.11.
NMR: $\delta$=5.64–5.23(2H, m), 4.67(2H, m), 4.56(1H, m), 4.0(1H, m).
IR: $\nu$=3650–3200, 2930, 2860, 1710, 1450, 1350, 1260, 1200, 1130, 1120 cm$^{-1}$.
MS: m/e=521, 504, 488, 435, 419, 403, 384.

REFERENCE EXAMPLE 4

1,11α,15S-tris(tetrahydropyran-2-yloxy)-15-(3RS-propyl-1S-cyclopentyl)-16,17,18,19,20-pentanorprost-trans-13-ene-6,9-dione A solution of 0.478 g of 1,11α,15S-tris(tetrahydropyran-2-yloxy)-9α-hydroxy-15-(3RS-propyl-1S-cyclopentyl)-16,17,18,19,20-pentanorprost-trans-13-en-6-one (prepared in Reference Example 3) in 8 ml of acetone was cooled to −30° C., and to the solution, Jones reagent (2.6M) was added dropwise with monitoring by TLC. 1.5 ml of Jones reagent was added during reaction for 1 hr. After the reaction, the solution was quenched with isopropanol, and the solution was extracted with diethyl ether. The extract was washed successively with water, an aqueous solution of sodium bicarbonate, and a saturated aqueous solution of sodium chloride, dried over anhydrous magnesium sulphate and concentrated uner reduced pressure. The residue was purified by column chromatography on silica gel using a mixture of cyclohexane and ethyl acetate (5:1→4:1) as eluent to give 0.354 g of the title compound, in a 74.2% yield having the following physical characteristics:

TLC (cyclohexane:ethyl acetate=1:1): Rf=0.43.
NMR: $\delta$=5.8–5.3(2H, m), 4.8–4.5(3H, m), 0.9(3H, m).
IR: $\nu$=1743, 1714, 1032, 973 cm$^{-1}$.
MS: m/e=561, 544, 460, 442, 358.

The following compounds were obtained by the same procedure as Reference Example 4;

(a)

1,11α,15S-tris(tetrahydropyran-2-yloxy)-15-(3RS-butyl-1S-cyclopentyl)-16,17,18,19,20-pentanorprost-trans-13-ene-6,9-dione Starting material: 0.472 g of 1,11α,15S-tris-(tetrahydropyran-2-yloxy)-15-(3RS-butyl-1S-cyclopentyl)-16,17,18,19,20-pentanorprost-trans-13-en-6-one (prepared in Reference Example 3(a));

Yield: 0.365 g (77.5%).
TLC (cyclohexane:ethyl acetate=2:1): Rf=0.24.
NMR: $\delta$=5.8–5.2(2H, m), 4.85–4.5(3H, m), 0.89(3H, m).
IR: $\nu$=1743, 1710, 1032, 974 cm$^{-1}$.
MS: m/e=558, 474, 456, 390, 372, 354.

REFERENCE EXAMPLE 5

1,11α,15S-tris(tetrahydropyran-2-yloxy)-15-cyclopentyl-16,17,18,19,20-pentanorprost-trans-13-ene-6,9-dione To a mixture of 2.67 ml of pyridine and 50 ml of methylene chloride, 1,65 g of chromium trioxide and 8 g of CELITE (registered trade mark:diatomaceous earth) were added at room temperature, and the mixture was stirred for 5 min and then cooled to about 3° C. To the solution obtained, a solution of 500 mg of 1,11α,15S-tris(tetrahydropyran-2-yloxy)-9α-hydroxy-15-cyclopentyl-16,17,18,19,20-pentanorprost-trans-13-en-6-one (prepared in Reference Example 3(b)) in 6 ml of methylene chloride, was added dropwise over a period of 7 min. After stirring for 15 min, 7.62 g of sodium hydrosulphate monohydrate was added to the solution, and the mixture was stirred for 2 min. The mixture was filtered and the residue was washed with 200 ml of methylene chloride. The combined filtrate and washing was dried over anhydrous magnesium sulfate, and concentrated under reduced pressure. The residue was purified by column chromatography twice on silica gel using mixtures of cyclohexane and ethyl acetate [(3:1) and (5:1)] as eluent to give 312 mg of the title compound, in a 62.6% yield, having the following physical characteristics:

TLC (cyclohexane:ethyl acetate=1:1): Rf=0.46.
NMR: $\delta$=5.68(2H, m), 4.7(2H, m), 4.56(1H, m).
IR: $\nu$=2940, 2860, 1740, 1710, 1450, 1350, 1260, 1240, 1200, 1130, 1110 cm$^{-1}$.
MS: m/e=604(M+), 519, 502, 451, 418, 400, 367.

EXAMPLE 1

2-decarboxy-2-hydroxymethyl-6-oxo-15-(3RS-propyl-1S-cyclopentyl)-16,17,18,19,20-pentanor-PGE$_1$ [i.e. 11α,15S-dihydroxy-6,9-dioxo-15-(3RS-propyl-1S-cyclopentyl)-16,17,18,19,20-pentanorprost-trans-13-en-1-ol]

A mixture of 0.332 g of 1,11α,15S-tris(tetrahydropyran-2-yloxy)-15-(3RS-propyl-1S-cyclopentyl)-16,17,18,19,20-pentanorprost-trans-13-ene-6,9-dione (prepared in Reference Example 4), 0.6 ml of tetrahydrofuran and 6 ml of an aqueous 65% solution of acetic acid was stirred for 2 hrs at 80° C. Ethyl acetate was added to the mixture. The oily layer which separated was washed successively with water, an aqueous solution of sodium bicarbonate, and a saturated aqueous solution of sodium chloride, dried over anhydrous magnesium sulphate, and concentrated under reduced pressure. The residue was purified by column chromatography on silica gel [eluent: a mixture of ethyl acetate and cyclohexane (4:1)→ethyl acetate containing 1% ethanol] to give 63 mg of the title compound, in a 31% yield, having the following physical characteristics:

TLC (ethyl acetate:formic acid=400:5): Rf=0.16.
mp: 63.0°–65.0° C.
NMR: $\delta$=5.58(2H, m), 4.10(1H, m), 3.83(1H, m), 3.63(2H, t), 2.9–2.6(2H, m), 0.88(3H, m).
IR(KBr tablet): $\nu$=3440, 1746, 1710, 1070, 972 cm$^{-1}$
MS: m/e=394(M+), 376, 358, 340, 265, 247.

The following compounds were obtained by the same procedure as Example 1.

(a)

2-decarboxy-2-hydroxymethyl-6-oxo-15-(3RS-butyl-1S-cyclopentyl)-16,17,18,19,20-pentanor-PGE$_1$ [i.e. 11α,15S-dihydroxy-6,9,dioxo-15-(3RS-butyl-1S-cyclopentyl)-16,17,18,19,20-pentanorprost-trans-13-en-1-ol]

Starting material: 0.345 g of 1,11α,15S-tris-(tetrahydropyran-2-yloxy)-15-(3RS-butyl-1S-cyclopentyl)-16,17,18,19,20-pentanorprost-trans-13-ene-6,9-dione (prepared in Reference Example 4(a));

Yield: 0.117 g (54.7%).

TLC (ethyl acetate:formic acid=400:5): Rf=0.18.
mp: 92°–95° C.;
NMR: $\delta$=5.6(2H, m), 4.10(1H, q), 3.84(1H, q), 3.64(2H, t), 2.79(1H, dd), 2.70(1H, m), 0.89(3H, t).
IR(KBr tablet): $\nu$=3420, 1747, 1710, 975 cm$^{-1}$.
MS: m/e=390, 372, 364, 265, 247.

(b)
2-decarboxy-2-hydroxymethyl-6-oxo-15-cyclopentyl-16,17,18,19,20-pentanor-PGE$_1$ [i.e. 11$\alpha$,15S-dihydroxy-6,9-dioxo-15-cyclopentyl)-16,17,18,19,20-pentanorprost-trans-13-en-1-ol]

Starting material: 300 mg of 1,11$\alpha$,15S-tris-(tetrahydropyran-2-yloxy)-15-cyclopentyl-16,17,18,19,20-pentanorprost-trans-13-ene-6,9-dione (prepared in Reference Example 5);

Yield: 96 mg (54.5%; purified by recrystallization, twice, from mixtures of hexane and ethyl acetate, and cyclohexane and ethyl acetate, after column chromatography.).

TLC (ethyl acetate:formic acid=400:5): Rf=0.13.
mp: 84°–86° C.
NMR: $\delta$=5.64(1H, dd), 5.52(1H, dd), 4.1(1H, q), 3.83(1H, t), 3.64 (2H, t), 3.0–2.6(6H, m), 2.6–2.3 (5H, m), 2.05–1.1(15H, m).
IR(KBr tablet): $\nu$=3600–3100, 2940, 2850, 1740, 1710, 1400, 1350, 1300, 1230, 1060 cm$^{-1}$.

The present invention includes within its scope pharmaceutical compositions which comprise at least one prostaglandin analogue of general formula (I) or cyclodextrin clathrate thereof, together with a pharmaceutical carrier or coating.

In clinical practice, for the treatment of cyto-damage or gastric ulceration, the compounds of the present invention will normally be administered systemically or partially; usually by oral or parenteral (.e.g. intravenous, subcutaneous or intramuscular) administration.

Solid compositions for oral administration include compressed tablets, pills, dispersible powders, and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents, e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorble material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations according to the invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark). These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solids compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, symptoms, the desired therapeutic effects, the route of administration, and the duration of the treatment.

In the human adult, the doses per person are generally between 0.1 and 100 $\mu$g, preferably between 1 and 50 $\mu$g by oral administration, and between 0.01 and 50 $\mu$g, preferably between 0.1 and 20 $\mu$g by parenteral administration in the treatment of cyto-damage, and can be administered up to several times per day.

As mentioned above, the doses to be used depend on various conditions. Therefore, there may be cases in which doses greater than the range specified above, or lower than the ranges specified above, may be used.

The following Examples illustrate pharmaceutical compositions according to the invention.

EXAMPLE 2

To a mixture of 3 mg of 2-decarboxy-2-hydroxymethyl-6-oxo-15-(3RS-propyl-1S-cyclopentyl)-16,17,18,19,20-pentanor-PGE$_1$, 100 mg of magnesium stearate, 20 mg of silicon dioxide, 10 mg of talc and 200 mg of cellulose gluconate (CCG), microcrystalline cellulose was added to obtain 10 g of mixture. After mixing well, the mixture was punched out in conventional manner to obtain 100 tablets each containing 30 $\mu$g of the active ingredient.

EXAMPLE 3

To 3 mg of 2-decarboxy-2-hydroxymethyl-6-oxo-15-(3RS-propyl-1S-cyclopentyl)-16,17,18,19,20-pentanor-PGE$_1$, lactose was added to obtain 21 g of mixture. After mixing well, the powder obtained was machine filled into 100 No. 3 gelatin capsules each containing 30 μg of the active ingredient.

EXAMPLE 4

A solution of 30 mg of 2-decarboxy-2-hydroxymethyl-6-oxo-15-(3RS-propyl-1S-cyclopentyl)-16,17,18,19,20-pentanor-PGE$_1$ dissolved in 10 ml of chloroform was added to 100 ml of MCT (a mixture of triglycerides of fatty acids containing from 8 to 10 carbon atoms) and the solution was mixed well. After removing chloroform under reduced pressure, the residue was machine filled into 100 soft capsules each containing 30 μg of the active ingredient.

EXAMPLE 5

6 mg of α-cyclodextrin clathrate of 2-decarboxy-2-hydroxymethyl-6-oxo-15-(3RS-propyl-1S-cyclopentyl)-16,17,18,19,20-pentanor-PGE$_1$ (prepared by known methods; containing 500 μg of active ingredient) was dissolved in 300 ml of distilled water for injection. The solution was sterilized in conventional manner and placed in 3 ml portions in 5 ml ampoules to obtain 100 ampoules each containing 5 μg of the active ingredient.

EXAMPLE 6

Tablets, capsules, soft capsules and solutions for injection were prepared using the compounds of Example 1(a) and 1(b) as an active ingredient, in the same manner as described in Example 2, 3, 4 and 5.

We claim:

1. Prostaglandin E$_1$ analogues of the formula:

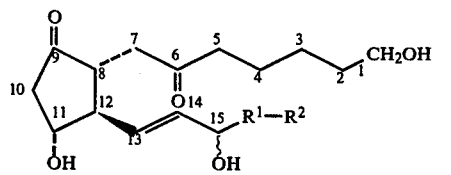

(I)

(wherein R$^1$ represents a single bond or a straight- or branched-chain alkylene group of from 1 to 5 carbon atoms, R$^2$ represents a cycloalkyl group of from 4 to 7 carbon atoms either unsubstituted or substituted by at least one straight- or branched-chain alkyl group of from 1 to 8 carbon atoms, and the double bond between C$_{13}$ and C$_{14}$ is trans), or a cyclodextrin clathrate thereof.

2. A compound according to claim 1 wherein the grouping R$_1$—R$^2$ is a cyclobutyl, cyclopentyl, 3-methylcyclopentyl, 3-ethylcyclopentyl, 3-propylcyclopentyl, 3-butylcyclopentyl, 3-pentylcyclopentyl, cyclohexyl or 4-propylcyclohexyl group.

3. A compound according to claim 1 wherein the grouping R$^1$—R$^2$ is a cyclopentyl, 3-methylcyclopentyl, 3-ethylcyclopentyl, 3-propylcyclopentyl, 3-butylcyclopentyl or 3-pentylcyclopentyl group.

4. A compound according to claim 1 wherein the hydroxy group attached to the 15-position is in α-configuration.

5. A compound according to claim 1 which is 2-decarboxy-2-hydroxymethyl-6-oxo-15-(3propylcyclopentyl)-16,17,18,19,20-pentanor-PGE$_1$ or a cyclodextrin clathrate thereof.

6. A compound according to claim 1 which is 2-decarboxy-2-hydroxymethyl-6-oxo-15-(3-butylcyclopentyl)-16,17,18,19,20-pentanor-PGE$_1$ or a cyclodextrin clathrate thereof.

7. A compound according to claim 1 which is 2-decarboxy-2-hydroxymethyl-6-oxo-15-cyclopentyl-16,17,18,19,20-pentanor-PGE$_1$ or a cyclodextrin clathrate thereof.

8. A pharmaceutical composition useful in the treatment or prevention of cytodamage which comprises, as active ingredient, an effective amount of a prostaglandin E$_1$ analogue as claimed in claim 1, or cyclodextrin clathrate thereof.

9. A pharmaceutical composition according to claim 8, which comprises, as active ingredient, a compound selected from the group consisting of 2-decarboxy-2-hydroxymethyl-6-oxo-15-(3-propylcyclopentyl)-16,17,18,19,20-pentanor-PGE$_1$, 2-decarboxy-2-hydroxymethyl-6-oxo-15-(3-butylcyclopentyl)-16,17,18,19,20-pentanor-PGE$_1$ or 2-decarboxy-2-hydroxymethyl-6-oxo-15-cyclopentyl-16,17,18,19,20-pentanor-PGE$_1$ or a cyclodextrin clathrate thereof.

10. A method for the prevention or treatment of cytodamage in a mammalian host which comprises administering to a host subject to or suffering from cytodamage, an effective amount of a prostaglandin E$_1$ analogue as claimed in claim 1, or cyclodextrin clathrate thereof.

11. A compound of the formula:

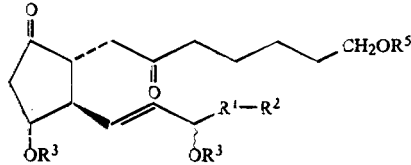

wherein R$^3$ represents a tetrahydropyran-2-yl or tetrahydrofuran-2-yl group, either unsubstituted or substituted by at least one alkyl group, or a 1-ethoxyethyl group, R$^5$ represents a tetrahydropyran-2-yl or tetrahydrofuran-2-yl group, either unsubstituted or substituted by at least one alkyl group, or a 1-ethoxyethyl group, or a triphenylmethyl group, and the other symbols are as defined in claim 1.

* * * * *